(12) United States Patent
Hilal

(10) Patent No.: US 7,740,625 B2
(45) Date of Patent: Jun. 22, 2010

(54) SURGICAL DIGITIZING APPARATUS AND METHOD

(75) Inventor: Said S. Hilal, Coto de Caza, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1249 days.

(21) Appl. No.: 10/512,425

(22) PCT Filed: Feb. 10, 2003

(86) PCT No.: PCT/US03/04007

§ 371 (c)(1),
(2), (4) Date: Oct. 20, 2004

(87) PCT Pub. No.: WO03/090608

PCT Pub. Date: Nov. 6, 2003

(65) Prior Publication Data

US 2005/0222561 A1 Oct. 6, 2005

Related U.S. Application Data

(60) Provisional application No. 60/375,314, filed on Apr. 24, 2002.

(51) Int. Cl.
*A61B 18/18* (2006.01)
(52) U.S. Cl. .......................... 606/1; 600/393; 600/547; 606/34
(58) Field of Classification Search ............. 606/32–52, 606/1; 607/91–108; 600/393, 547
See application file for complete search history.

(56) References Cited

U.S. PATENT DOCUMENTS

| | | | | |
|---|---|---|---|---|
| 5,172,699 A | * | 12/1992 | Svenson et al. | 600/518 |
| 5,741,298 A | * | 4/1998 | MacLeod | 606/213 |
| 5,846,196 A | * | 12/1998 | Siekmeyer et al. | 600/374 |
| 6,032,673 A | * | 3/2000 | Savage et al. | 128/898 |
| 6,071,281 A | | 6/2000 | Burnside et al. | |
| 6,308,097 B1 | * | 10/2001 | Pearlman | 600/547 |
| 6,330,479 B1 | * | 12/2001 | Stauffer | 607/101 |
| 6,425,895 B1 | * | 7/2002 | Swanson et al. | 606/41 |
| 6,494,882 B1 | * | 12/2002 | Lebouitz et al. | 606/45 |
| 6,595,990 B1 | * | 7/2003 | Weinstein et al. | 606/41 |
| 6,645,197 B2 | * | 11/2003 | Garrison et al. | 606/1 |
| 6,845,264 B1 | * | 1/2005 | Skladnev et al. | 600/547 |
| 6,980,852 B2 | * | 12/2005 | Jersey-Willuhn et al. | 600/547 |
| 7,210,817 B2 | * | 5/2007 | Lee et al. | 362/249 |

* cited by examiner

*Primary Examiner*—Lee S Cohen
(74) *Attorney, Agent, or Firm*—Patrick Y. Ikehara; John F. Heal; Kenneth K. Vu

(57) ABSTRACT

A surgical digitizing apparatus and procedure will typically involve a pad having discrete segments which may be arranged in a specific order to accommodate a particular procedure. The individual segments can then be used to accomplish both diagnostic and therapeutic functions. For example, the segments can be interrogated to produce a map of body tissue and then electrosurgically energized to perform a therapeutic function in accordance with the map. Communication with the discrete segments will typically be accomplished through a microprocessor and associated switching circuits.

14 Claims, 5 Drawing Sheets

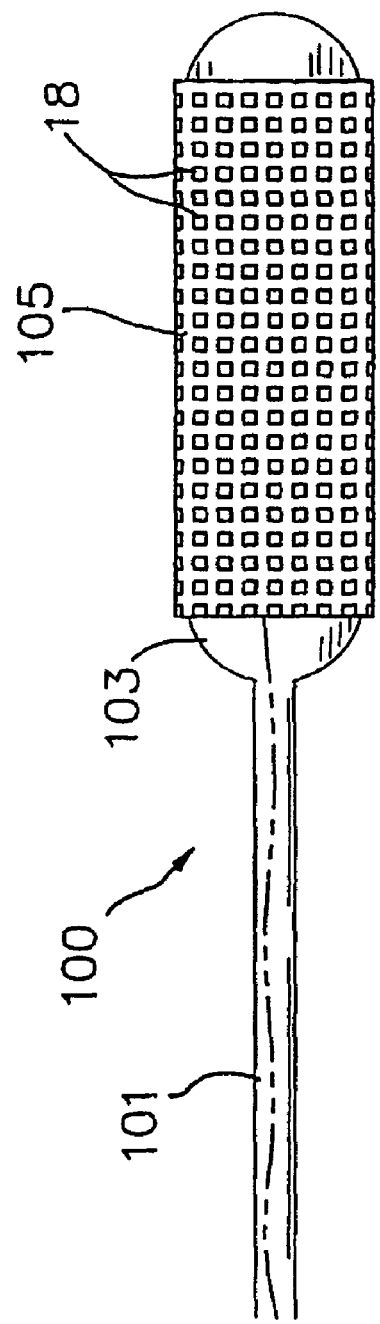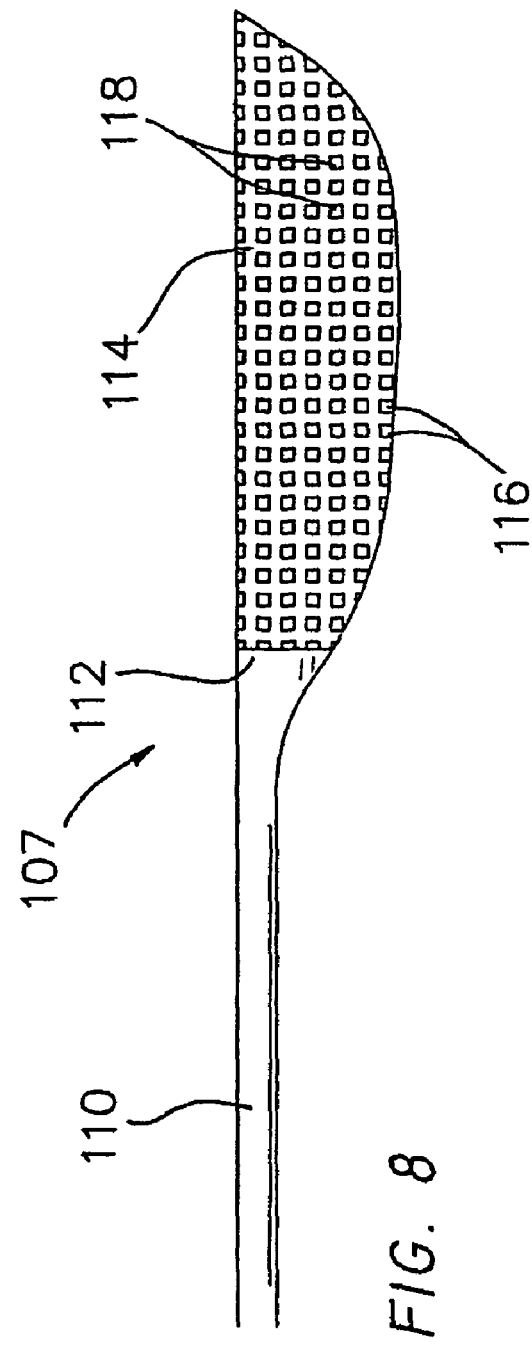

SURGICAL DIGITIZING APPARATUS AND METHOD

CROSS-REFERENCES TO RELATED APPLICATIONS

This application is a 371 filing of PCT/US03/04007, filed Feb. 10, 2003, which claims priority from U.S. provisional application Ser. No. 60/375,314, filed Apr. 24, 2002.

FIELD OF THE INVENTION

This invention relates generally to methods and apparatus for digitizing diagnostic and therapeutic surgical procedures.

BACKGROUND OF THE INVENTION

In the distant past, surgery was performed by a surgeon who would typically open a patient in order to visualize and diagnose the operation and function of internal organs. Visualization through this open procedure might indicate the presence of a tumor, for example. At this point, the surgeon would undertake the indicated therapy, such as removal of the tumor.

More recently, new technologies and automation have greatly increased the diagnostic function of the surgeon. Notably, non-invasive visualization techniques are now available through X-ray fluoroscopy and magnetic imaging which can aid in the location and diagnosis of anatomical problems. With automated procedures, the same diagnosis or therapy can typically be reproduced to offer the safest and most effective procedure regardless of variations in the knowledge and skill of the surgeon.

Notwithstanding this automation of diagnostic procedures, the actual therapy required has continued to rely on the knowledge and skill of the surgeon who is operating increasingly with small mechanical devices such as clips, clamps, scalpels, retractors, and needles, for example. With one exception, the therapeutic procedures have not been particularly automated so they continue to rely heavily on the subjective knowledge and skill of the surgeon.

The one exception, which uses electrosurgical energy to cut, coagulate, or fulgurate tissue, highlights some of the advantages of modern technology. This procedure involves the use of electrosurgical energy to cut, coagulate, or fulgurate tissue. Evolution of this technology has produced sophisticated electrosurgical generators that offer a high degree of control over voltage and frequency. With appropriate variations in these parameters, signals can now be developed which are adapted for a particular purpose, such as cutting or coagulation, as well as a particular patient.

Notwithstanding these advances in the production of electrosurgical signals, the delivery of those signals has remained highly subjective to the knowledge and skill of the surgeon. Thus, the electrosurgical energy must be delivered through a handpiece that is moved over a desired area while a precise distance of separation between the handpiece and the tissue is maintained. In this latter regard, contact between the handpiece and the tissue to be avoided; rather, a slight spacing is beneficial as it promotes the desired sparking associated with the electrosurgical effect. Although much teaching has been devoted to train surgeons in these procedures, there continues to be a wide variation in the knowledge and skill implementing this therapeutic procedure.

SUMMARY OF THE INVENTION

In accordance with the present invention, many of these deficiencies of the past are overcome with an automated apparatus and method for conducting both diagnostic and therapeutic procedures. This concept involves a digitizing pad including a multiplicity of discrete segments which can be energized or interrogated individually or in patterns. Thus, diagnosis can be conducted on an individual segment or pattern basis in order to initially provide the surgeon with information prior to any therapeutic activity. Diagnosis throughout the pad can provide appropriate mapping, for example, as to the location of tissue and bone.

Once an appropriate diagnosis is made, the segments of the digitizing pad can be individually activated as appropriate to accomplish the therapeutic purpose. This segment activation can be provided through monopolar or bipolar application of electrosurgical signals delivered, for example, simultaneously or sequentially to a section or pattern on the pad. Specific pads can be prepared for specific surgeries wherein only certain patterns are offered. These specific pads can also be adapted for use with other instruments. The pads can be made either reusable or disposable. Furthermore, a specific pad may be created where individual segments are sacrificed during the therapeutic application in which case the pad is rendered functional for only a single use.

The pad provides for immediate availability of the electrosurgical power, the application of which can be controlled through a microprocessor. The pad can also be adapted for use to facilitate visualization. CCD cameras can be provided in the individual segments or in the pad as a whole. Also, lights can be provided in the pad to provide the surgeon with a visual indication of segmented diagnostic or therapeutic functions.

These and other features and advantages of the invention will become more apparent with a description of preferred embodiments and sequence to the associated drawings.

DESCRIPTION OF THE DRAWINGS

FIG. 7 is a side elevation view of a catheter having an inflatable balloon covered with a digitizing pad of the present invention; and FIG. 8 is a side elevation view of a scalpel adapted to carry a digitizing pad of the present invention.

DESCRIPTION OF THE INVENTION

Figure 1:
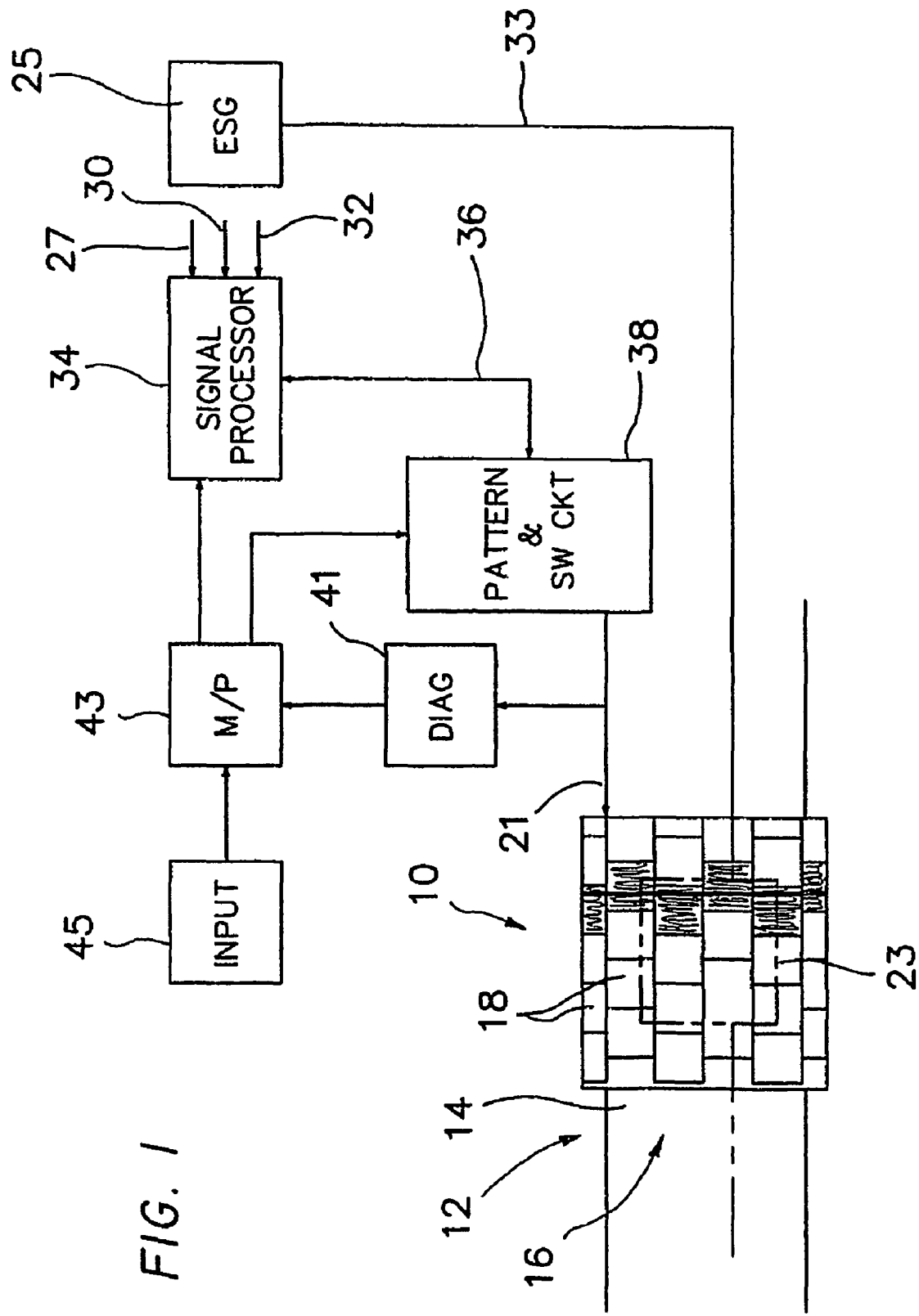
FIG. 1 is a top plan view of a digitizing pad operatively disposed on the abdomen of a patient with associated diagnostic and therapeutic electronics shown schematically.

A digitizing pad is illustrated in FIG. 1 and designated by the reference numeral 10. The pad 10 is illustrated in an operative disposition relative to a body wall of a patient 12. In this case, the body wall is an abdominal wall 14 which defines an abdominal cavity 16 of the patient 12. Of course the pad 10 could be applied to other body walls, both interiorly and exteriorly of the patient 12.

The pad 10 will generally have a planar configuration and may be rigid, although a preferred embodiment is contemplated where the pad is flexible and therefore capable of being placed in contact with a curved surface of the body wall such as the abdominal wall 14. The pad 10 may also be adapted for placement on a probe or handle facilitating movement of the pad relative to the patient 12.

The pad 10 is configured with individual or discrete segments 18, each of which may be adapted to perform a diagnostic and/or therapeutic function. Appropriate electrical connections are provided for each of the segments 18 and combined in a single output/input cable 21. As noted in greater detail below, these segments 18 can be arranged in individual sections or patterns, such as the pattern encompassed by line 23, to facilitate a particular diagnostic or therapeutic function.

In the illustrated embodiment, the pad 10 is specifically adapted for use in an electrosurgical application. An electrosurgical generator 25 is provided and presents three generic signals for cutting, coagulation, and fulguration on three output lines 27, 30, and 32, respectively. These signals can be introduced to a signal processor 34 to further modify the generic signal as required for a particular patient. The resulting signal can be introduced on a line 36, into a pattern and switching circuit 38. The signal from the processor 34 can then be introduced through the cable 21 to the segments 18 simultaneously or sequentially as determined by the pattern and switching circuit 38.

In the illustrated embodiment, these are the active elements of a therapeutic function which results from the application of electrosurgical energy to the tissue of the patient 12. But the pad 10 also is adapted to perform a diagnostic function which typically will precede the therapeutic function. The diagnostic elements will typically include a diagnostic circuit 41 which receives information or feedback from the discrete segments 18. This information, which can be communicated through the cable 21, is introduced into a microprocessor 43 having an input device such as a keyboard 45.

Figure 2:
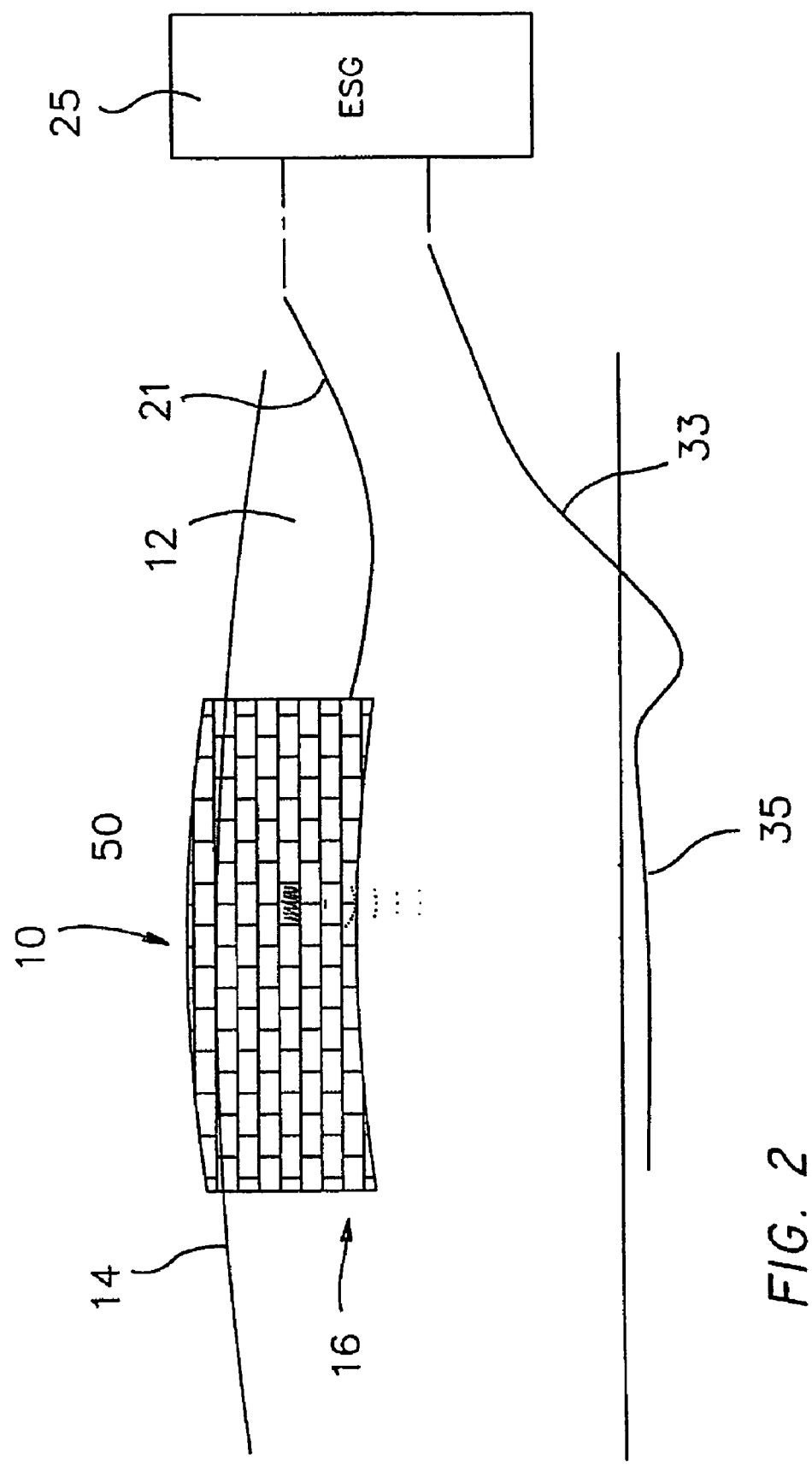
FIG. 2 is a side elevation view of the digitizing pad operatively disposed on the abdomen of the patient in a monopolar electrosurgical procedure.

A further discussion of the electrosurgical function is facilitated with reference to FIG. 2, which provides a side elevation view of the pad 10 on the abdomen 14 of the patient 12. It is well known that the delivery of an electrosurgical signal requires two poles or electrodes between which the electrosurgical energy passes. In a monopolar configuration, such as that illustrated in FIG. 2, a base plate 35 provides one of the poles and is connected ultimately to the electrosurgical generator 25 through a cable 33. The other pole would be provided by the discrete segments 18 of the pad 10 which can be energized simultaneously or sequentially through the cable 21.

For example, in FIG. 2, a particular segment is designated by the reference numeral 50. Energy introduced to this segment 50 is applied to the tissue or the skin of the patient 12 at a very small area resulting in a high current density or concentration. At this small area, the electrosurgical effect of cutting, coagulation or fulguration is produced. From this small area, the current passes through the body of the patient 12 to the large area of the base plate 35 where the energy is sufficiently disbursed that there is very little current density and no electrosurgical effect.

Figure 3:
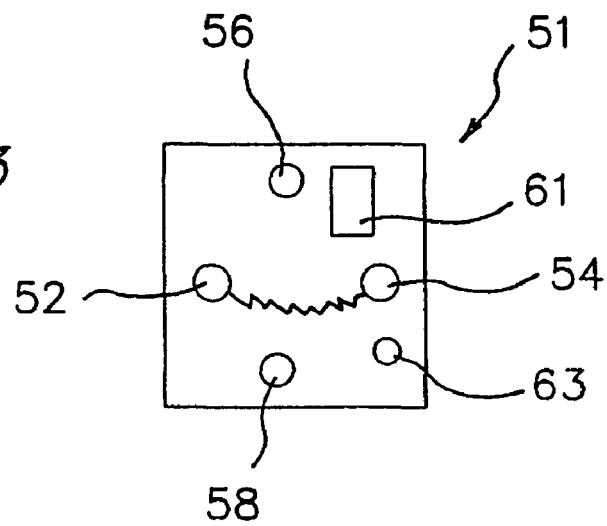
FIG. 3 is a top plan view of an individual segment of the digitizing pad showing electrodes and sensors adapted for both diagnostic and therapeutic purposes.

In a bipolar configuration, an individual segment designated 51 in FIG. 3, may be provided with two electrodes, 52 and 54. With this configuration the electrosurgical path is drawn only within the small area of the segment 51. Alternatively, two separate segments 18 could provide the two poles of a bipolar configuration.

Other electrodes 56 and/or sensors 58 can be provided in the individual segment 51 for diagnostic purposes. A camera 61 or light 63 could also be provided in the segment 51 to facilitate interior and/or exterior visualization.

Given this specific adaptation of the digitizing pad 10 for electrosurgical applications, a discussion of a typical method of operation can now be undertaken. After the pad 10 is initially placed relative to the operative site, the cables 21 and 33 can be connected. In a particular procedure this may be the last active step of the surgeon at the operative site before removing the pad 10. It is contemplated that the surgeon will perform his expertise at the keypad 45, effectively directing the diagnosis and therapeutic functions through the microprocessor 43.

Initially, diagnosis may be undertaken by activating a diagnostic electrode 56 or sensors 58 in order to define the precise environment of the operative site. For example, conductivity of the tissue at each segment 18 may be of interest, as well as other physical parameters such as pressure. With appropriate feedback from the electrode 56 or sensor 58, the diagnostic circuit 41 (FIG. 1) would provide a mapping indication or other information to the microprocessor 43.

In additional to this mapping function, a preferred line of cutting, for example, may be displayed on a computer screen or by the visualization light 63 on the segment 18 of the pad 10. Following this diagnosis, appropriate electrosurgical cutting can be undertaken through the pattern and switching circuit 38 on appropriate command and direction from the microprocessor 43.

Figure 4:
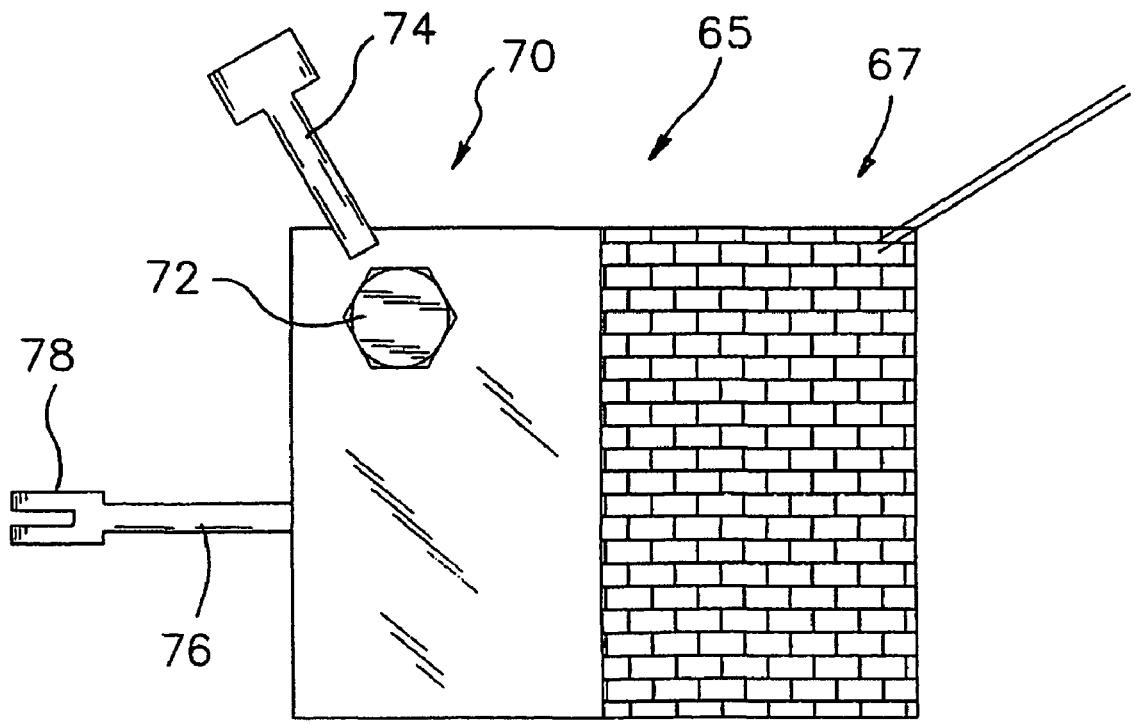
FIG. 4 is a top plan view of a specific digitizing pad adapted for use in a specific diagnostic and/or therapeutic procedure.

It will be apparent that the pad 10 can be manufactured for repeated use and adapted through the software associated with the microprocessor 43 to perform many types of diagnostic and therapeutic functions as appropriate for a particular surgical operation. Alternatively, individual pads such as that illustrated by the reference numeral 65 in FIG. 4 can be adapted for specific surgical procedures. This specific pad 65 has several different sections such as a segmented portion 67 and a non-segmented portion 70. The segmented portion 67 could operate for both diagnostic and therapeutic purposes in the manner previously disclosed. The non-segmented portion 70 may include an access device 72, such as a gel seal of the general type disclosed and claimed in U.S. Provisional Patent Application Ser. No 60/241,958 filed on Oct. 19, 2000, entitled "Hand Assisted Laparoscopic Apparatus and Method"; and PCT Application Serial No. PCT/US01/29682, filed on Sep. 21, 2001, entitled "Surgical Access Apparatus and Method"; and PCT Application Serial No. PCT/US01/50160 filed Oct. 19, 2001, entitled "Sealed Surgical Access Device" which are incorporated herein by reference. Including the seal 72 in specific pad 65 would provide a site on the pad 65 which is adapted for introduction of a surgical instrument, such as a trocar 74. Other types of surgical instruments could be provided with the specific pad 65 in order to accommodate all of the functions associated with a specific operative procedure. Some of these elements could be fixed to the pad 65, such as the seal 72. Others might merely be removably attached to the pad 65, for example, by a lanyard 76 holding a clamp 78.

Figure 5:
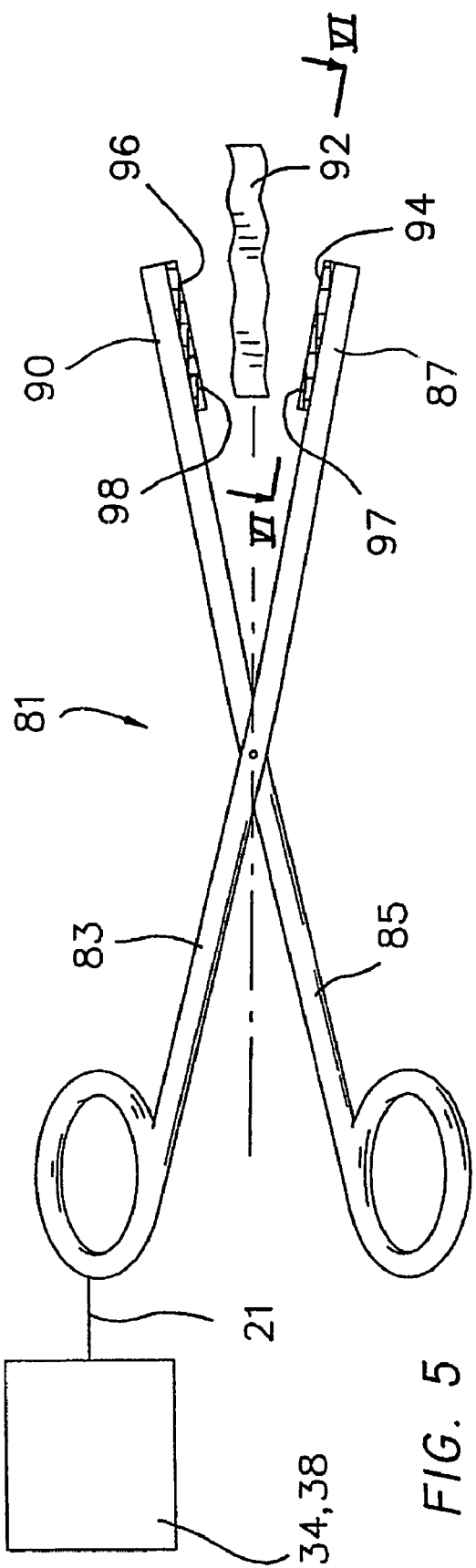
FIG. 5 is a side elevation view of a grasper having a pair of jaws carrying at least one digitizing pad of the present invention.

It will be apparent from the foregoing discussion that the digitizing pad 10 can be incorporated into many surgical devices in order to automate and otherwise increase the safety and efficacy of a particular surgical procedure. For example, a grasper 81 is illustrated in FIG. 5 to include a pair of scissor handles 83 and 85. At the distal end of the handles 83 and 85, a pair of jaws 87 and 90, respectively, are operable between an open state, wherein the jaws 87 and 90 are separated, and a closed state wherein the jaws 87 and 90 are brought into close proximity on either side of tissue 92. The jaws 87 and 90 can each be provided with a digitizing pad 94 and 96, respectively. In operation, the jaws 87, 90 are initially opened to receive the tissue 92. Then the jaws 87, 90 are closed to bring the pads 94 and 96 into close proximity on either side of the tissue 92. At this point, the digitizing pads 94 and 96 can be interrogated or activated through the cable 21, to perform the desired diagnostic and/or therapeutic procedures.

The digitizing pads 94 and 96 in this embodiment may be similar or they may be different and complimentary in order to take advantage of their proximity on either side of the tissue 92. For example, bipolar electrosurgical effects can be undertaken by activating a particular segment 97 on the pad 94 with a positive charge, and simultaneously activating a complementary segment 98 on the pad 96 with a negative charge. Other complimentary complementary functions can be accommodated with the two digitizing pads 94, 96 disposed in this opposing relationship, which most commonly occurs with surgical instruments having opposing jaws, such as clips, clamps and scissored instruments such as the grasper 81.

Figure 6:
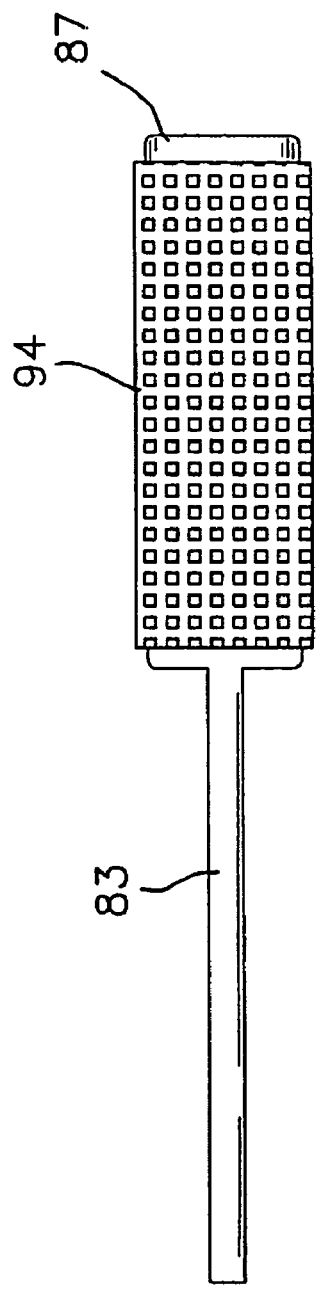
FIG. 6 is a top elevation view of one of the jaws taken along the lines VI-VI of FIG. 5.

A top plan view of the jaw 87 is illustrated in FIG. 6 and taken along the lines VI-VI of FIG. 5. This view more directly illustrates a preferred disposition of the pad 94 on the jaw 87. When the pad 94 is attached to the jaw 87 or other carrier, it can be made removable in which case different pads can be used to accomplish different functions with the surgical instrument, such as the grasper 81.

Another carrier for the pad 10 might include a catheter 98 as illustrated in FIG. 7. In this embodiment, the catheter 100 includes a catheter shaft 101 as well as an inflatable balloon 103. It is contemplated that a pad 105 could be carried by the inflatable balloon 103 and moved into proximity with conduit tissue by inflation of the balloon 103. Again, the digitizing segments 18 could be activated in a particular physical pattern and/or a particular order to accomplish both diagnostic and therapeutic functions. Note that in this and several other embodiments, the pad 105 could be defined by the discrete segments 18 individually adhered to the surface of the balloon 103.

A scalpel is illustrated in FIG. 8 and designated by the reference numeral 107. The scalpel 107 includes a handle 110 as well as a blade 112, with a digitizing pad 114 carried by the blade 112. The scalpel 107 is representative of any surgical instrument that could be used as a carrier for the pad 114. In these instruments the electrosurgical functions may be of primary interest. With respect to the scalpel 107, those digitizing segments 116 which are disposed near the edge of the blade 112 could be energized to perform a cutting function. Digitizing segments 118 disposed along the sides of the blade 112 might be energized to perform a coagulation function. Thus, the leading edge of the blade 112 would initially separate tissue while the sides of the blade 112 would coagulate the severed tissue.

Although the concept of this invention has been disclosed with reference to specific embodiments and a specific electrosurgical procedure, it will be apparent that the digitizing pad 10 can be adapted for many types of surgical systems which could benefit from discrete segments each adapted to perform some diagnostic or therapeutic function and capable of being interrogated or activated simultaneously or sequentially in a particular section or pattern.

The invention claimed is:

1. A method for digitizing an operative site on a patient to facilitate an operative procedure involving a tissue surface outside of a patient's body and defining interior regions of the operative site, comprising the steps of:

providing a pad having a plurality of discrete segments, each with characteristics for performing at least one of a diagnostic function and a therapeutic function associated with the operative procedure;

placing the pad outside of the patient's body on the tissue surface on the outside of the patient's body;

receiving information from the plurality of discrete segments to create a map of the interior regions of the operative site;

measuring tissue conductivity and pressure;

displaying the map on a computer screen;

activating a light on one of the plurality of discrete segments; and supplying the map to a microprocessor.

2. The method recited in claim 1, further comprising the steps of:

activating at least one of the plurality of discrete segments to perform the therapeutic function on the interior regions in a pattern dependent on the map.

3. The method recited in claim 1, further comprising the step of:

moving the pad and the plurality of discrete segments relative to the tissue surface to create the map with respect to a predetermined operative site.

4. The method recited in claim 1, wherein the placing step includes the step of moving the pad along the tissue surface on the outside of the patient's body.

5. The method recited in claim 1, further comprising the step of:

illuminating the operative site with a light carried by the pad.

6. A method for digitizing an operative site on a patient to facilitate an operative procedure involving a tissue surface outside of a patient's body and defining interior regions of the operative site, comprising the steps of:

providing a pad having a plurality of discrete segments, each with characteristics for performing at least one of a diagnostic function and a therapeutic function associated with the operative procedure;

placing the pad outside of the patient's body on the tissue surface on the outside of the patient's body;

receiving information from the plurality of discrete segments to create a map of the interior regions of the operative site; and introducing a surgical instrument through an access device carried by the pad;

wherein the access device carried by the pad comprises a gel seal carried by the pad.

7. A method for digitizing an operative site on a patient to facilitate an operative procedure involving a tissue surface outside of a patient's body and defining interior regions of the operative site, comprising the steps of:

providing a pad having a plurality of discrete segments, each with characteristics for performing at least one of a diagnostic function and a therapeutic function associated with the operative procedure;

placing the pad outside of the patient's body on the tissue surface on the outside of the patient's body;

receiving information from the plurality of discrete segments to create a map of the interior regions of the operative site;

measuring tissue conductivity and pressure;

displaying the map on a computer screen;

activating a light on one of the plurality of discrete segments;

supplying the map to a microprocessor; and activating at least one of the plurality of discrete segments to perform the therapeutic function on the interior regions in a pattern dependent on the map, wherein the activating step includes the step of electrosurgically activating at least one of the plurality of discrete segments.

8. The method recited in claim 7, further comprising the step of:
moving the pad and the plurality of discrete segments relative to the tissue surface to create the map with respect to a predetermined operative site.

9. The method recited in claim 7, wherein the placing step includes the step of moving the pad along the tissue surface on the outside of the patient's body.

10. The method recited in claim 7, further comprising the step of:
illuminating the operative site with the light on one of the plurality of discrete segments.

11. A method for digitizing an operative site on a patient to facilitate an operative procedure involving a tissue surface outside of a patient's body and defining interior regions of the operative site, comprising the steps of:
providing a pad having a plurality of discrete segments, each with characteristics for performing at least one of a diagnostic function and a therapeutic function associated with the operative procedure;
placing the pad outside of the patient's body on the tissue surface on the outside of the patient's body;
receiving information from the plurality of discrete segments to create a map of the interior regions of the operative site;
measuring tissue conductivity and pressure;
displaying the map on a computer screen;
activating a light on one of the plurality of discrete segments;
supplying the map to a microprocessor; and
activating at least one of the plurality of discrete segments to perform the therapeutic function on the interior regions in a pattern dependent on the map, wherein the activating step includes the step of electrosurgically activating at least one of the plurality of discrete segments in a bipolar configuration.

12. The method recited in claim 11, further comprising the step of:
moving the pad and the plurality of discrete segments relative to the tissue surface to create the map with respect to a predetermined operative site.

13. The method recited in claim 11, wherein the placing step includes the step of moving the pad along the tissue surface on the outside of the patient's body.

14. The method recited in claim 11, further comprising the step of:
illuminating the operative site with the light on one of the plurality of discrete segments.

* * * * *